(12) United States Patent
Kessler et al.

(10) Patent No.: US 11,352,729 B2
(45) Date of Patent: Jun. 7, 2022

(54) USE OF EXTERNAL INFORMATION IN THE OPERATION OF A HOUSEHOLD DEVICE

(71) Applicant: Henkel AG & Co. KGaA, Duesseldorf (DE)

(72) Inventors: Arnd Kessler, Monheim am Rhein (DE); Lars Zuechner, Langenfeld (DE); Robert Ruiz Hernandez, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 33 days.

(21) Appl. No.: 16/763,153

(22) PCT Filed: Dec. 13, 2018

(86) PCT No.: PCT/EP2018/084710
§ 371 (c)(1),
(2) Date: May 11, 2020

(87) PCT Pub. No.: WO2019/121302
PCT Pub. Date: Jun. 27, 2019

(65) Prior Publication Data
US 2020/0305678 A1    Oct. 1, 2020

(30) Foreign Application Priority Data
Dec. 19, 2017    (DE) .................... 10 2017 223 226.9

(51) Int. Cl.
*D06F 33/32*    (2020.01)
*A47L 15/00*    (2006.01)
(Continued)

(52) U.S. Cl.
CPC .......... *D06F 33/32* (2020.02); *A47L 15/0021* (2013.01); *A47L 15/0063* (2013.01);
(Continued)

(58) Field of Classification Search
CPC ........ G05B 19/042; G05B 2219/21109; G05B 2219/25258; G05B 2219/2633;
(Continued)

(56) References Cited

U.S. PATENT DOCUMENTS

| | | | | |
|---|---|---|---|---|
| 8,412,387 B2* | 4/2013 | Park | ........................ | H04L 69/04 700/297 |
| 8,942,835 B2* | 1/2015 | Gerdes | ..................... | D06F 34/05 700/90 |
| 8,984,692 B2* | 3/2015 | Balinski | .................. | D06F 33/43 8/158 |
| 9,207,270 B2* | 12/2015 | Caldeira | ................ | G06Q 50/06 |

(Continued)

FOREIGN PATENT DOCUMENTS

DE    102010063757 A1    6/2012
DE    102012200293 A1    7/2013
(Continued)

OTHER PUBLICATIONS

EPO, International Search Report issued in International Application No. PCT/EP2018/084710, dated Apr. 8, 2019.

*Primary Examiner* — Crystal J Barnes-Bullock
(74) *Attorney, Agent, or Firm* — Lorenz & Kopf, LLP (57) ABSTRACT

The present disclosure concerns a method for operating or controlling an operation of a household appliance (100, 300) performed by at least one device (100, 200, 300, 400). The method includes: obtaining external information representative of at least one external given situation outside the household appliance (100, 300); and operating or controlling an operation of the household appliance (100, 300) at least taking into account the external information obtained. In addition, the present disclosure concerns a device and a system for performing such a method.

15 Claims, 5 Drawing Sheets

(51) Int. Cl.
*G05B 19/042* (2006.01)
*G06Q 50/06* (2012.01)
*H04L 12/28* (2006.01)
*G16H 20/60* (2018.01)
*D06F 103/00* (2020.01)
*D06F 105/42* (2020.01)
*D06F 105/00* (2020.01)
*D06F 105/48* (2020.01)
*D06F 105/56* (2020.01)
*D06F 105/58* (2020.01)
*D06F 33/46* (2020.01)

(52) U.S. Cl.
CPC ........... *G05B 19/042* (2013.01); *G06Q 50/06* (2013.01); *H04L 12/2823* (2013.01); *A47L 2401/34* (2013.01); *A47L 2501/07* (2013.01); *D06F 33/46* (2020.02); *D06F 2103/00* (2020.02); *D06F 2105/00* (2020.02); *D06F 2105/42* (2020.02); *D06F 2105/48* (2020.02); *D06F 2105/56* (2020.02); *D06F 2105/58* (2020.02); *G05B 2219/21109* (2013.01); *G05B 2219/25258* (2013.01); *G05B 2219/2633* (2013.01); *G16H 20/60* (2018.01)

(58) Field of Classification Search
CPC .... G06Q 50/06; G16H 20/60; H04L 12/2823; A47L 15/0021; A47L 15/0063; A47L 2401/34; A47L 2501/07; D06F 33/32; D06F 33/46; D06F 2103/00; D06F 2105/00; D06F 2105/42; D06F 2105/48; D06F 2105/56; D06F 2105/58
See application file for complete search history.

(56) References Cited

U.S. PATENT DOCUMENTS

| | | | | |
|---|---|---|---|---|
| 9,451,031 | B2* | 9/2016 | Graziano | G05D 23/1931 |
| 9,927,777 | B2 | 3/2018 | Boeldt et al. | |
| 10,633,778 | B2* | 4/2020 | Park | H04L 12/2818 |
| 10,816,948 | B2* | 10/2020 | Davis, II | G06N 5/025 |
| 10,842,309 | B2* | 11/2020 | Koennings | G05B 15/00 |
| 11,005,942 | B2* | 5/2021 | Grossman, IV | H04L 67/125 |
| 11,093,554 | B2* | 8/2021 | Rexach | A61B 5/1072 |
| 11,099,540 | B2* | 8/2021 | Bradley | E03C 1/057 |
| 2010/0287709 | A1* | 11/2010 | Doyle | D06F 33/32 8/137 |
| 2011/0041562 | A1* | 2/2011 | Balinski | D06F 33/43 68/20 |
| 2011/0202293 | A1* | 8/2011 | Kobraei | G06Q 50/06 702/62 |
| 2013/0245841 | A1 | 9/2013 | Ahn et al. | |
| 2014/0148969 | A1* | 5/2014 | Graziano | G05D 23/1905 700/300 |
| 2014/0174489 | A1* | 6/2014 | Cottrell | A47L 15/0063 134/56 D |
| 2015/0094825 | A1 | 4/2015 | Kinoshita et al. | |
| 2017/0175317 | A1 | 6/2017 | Kim et al. | |
| 2017/0265706 | A1 | 9/2017 | Koven | |
| 2018/0034657 | A1* | 2/2018 | Brown | G06Q 10/0633 |
| 2021/0141353 | A1* | 5/2021 | Davis, II | G06Q 30/04 |
| 2021/0274000 | A1* | 9/2021 | Grossman, IV | G05B 15/02 |

FOREIGN PATENT DOCUMENTS

| | | | | |
|---|---|---|---|---|
| DE | 102012209751 A1 | 12/2013 | | |
| DE | 102012221119 A1 | 5/2014 | | |
| EP | 0509328 A2 | 10/1992 | | |
| EP | 0513539 A2 * | 11/1992 | | F25D 11/022 |
| EP | 1403998 A2 * | 3/2004 | | H02J 13/00 |
| EP | 1887443 A1 | 2/2008 | | |
| EP | 1403998 A3 * | 4/2012 | | H02J 13/00016 |

\* cited by examiner

USE OF EXTERNAL INFORMATION IN THE OPERATION OF A HOUSEHOLD DEVICE

CROSS-REFERENCE TO RELATED APPLICATION

This application is a U.S. National-Stage entry under 35 U.S.C. § 371 based on International Application No. PCT/EP2018/084710, filed Dec. 13, 2018, which was published under PCT Article 21(2) and which claims priority to German Application No. 10 2017 223 226.9, filed Dec. 19, 2017, which are all hereby incorporated in their entirety by reference.

TECHNICAL FIELD

The present disclosure concerns a method of operating or controlling the operation of a household appliance. In addition, the present disclosure also concerns a device, a system and computer program product.

BACKGROUND

From the state of the art, methods for operating or controlling the operation of household appliances, such as washing machines, are known. The aim of operating such household appliances is typically to achieve a high degree of user-friendliness and at the same time the best possible result (in the case of a washing machine, in particular, the most flawless cleaning result possible).

One approach to achieve a high degree of user-friendliness would be to optimize the user interface (input devices, output devices). If, for example, increased soiling is to be taken into account, the user must take this into account manually, for example, and select an appropriate program or detergent. Approaches are also conceivable in which device parameters are automatically adjusted in order to achieve the best possible result. For example, in the case of a washing machine, the program executed by the household appliance is adapted to the detergent used. This already improves the result, but ideally without the need for user intervention.

However, the disadvantage is that both the user-friendliness and the result to be achieved in this way still need improvement in many situations and scenarios.

Against this background, the present disclosure has the task of improving the result to be achieved with the household appliance with the highest possible degree of user-friendliness.

BRIEF SUMMARY

In an exemplary embodiment, a method for operating or controlling the operation of a household appliance, carried out by at least one device, is provided. The method includes:
  obtaining external information representative of at least one external condition outside the household appliance, and
  operating or controlling the operation of a household appliance at least in consideration of the external information received.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

By obtaining external information representative of (at least) one external condition outside the household appliance, this external information may be taken into account in operating or controlling the operation of the household appliance, which may be taken into account as a result of the additional external information provided by the household appliance compared to the information normally available, and the result to be achieved with the household appliance is improved.

By external information representative of at least one external condition is meant information which does not directly concern or is not representative of the internal operation of the household appliance. External information is therefore not (internal) information that typically (exclusively) characterizes the household appliance in question or the process carried out with it, but information that is typically available, determined and/or available independently of the household appliance in question. To give an example, in the case of a washing machine as a household appliance, the external information is not representative of the detergent or washing program used. Rather, the external information is representative of one or more factors or circumstances outside the household appliance which are not directly related to it.

An external condition outside the household appliance is, for example, a "surroundings condition", in particular a condition that exists or manifests itself in the apartment or house in which the household appliance is located. The external condition may therefore be a local condition in the vicinity of the cleaning device (for example, a few meters), such as room temperature. However, an external condition may also be a condition outside of enclosed areas or outdoors, such as a (local) weather condition. However, the external condition does not necessarily have to be a surroundings condition, but can also be an "activity situation" related in particular to the user of the household appliance, such as an activity of the user.

The external information may, for example, be in the form of digital data. Since the external information only needs to be representative of the external condition, the external information does not need to describe the external condition completely. The external information may also merely comprise or include information from which the external condition can be derived.

If required, the external information may also be representative of several external conditions outside the household appliance, which may then be taken into account in part or all of them when operating or controlling the operation of the appliance.

The external information may be obtained, for example, by receiving the external information at a communication interface of the appliance, for example via a (communication) network such as the Internet, a wired network and/or a wireless network.

In this example, the external information is received from a (remote) server. If the external information is, for example, representative of an external condition concerning the weather, the external information may be received, for example, from a server providing weather data.

Particularly preferred is the reception of external information as automated or automatic reception of external information. This means that the user does not have to provide or enter the external information manually (for example, via an input device of a user interface).

Operating or controlling the operation of the household appliance, by at least taking into account the external information received, means that the external information influences typical operating steps of the household appliance (if necessary). Such influence may, for example, include changing an operating mode of the household appliance, changing one or more process parameters of a method performed by the household appliance and/or adding or omitting method sections.

According to an embodiment of the method according to the first aspect, the household appliance is a laundry treatment machine (especially a tumble dryer, mangle or washing machine) and/or a cleaning machine (especially a washing machine or dishwasher). However, the term household appliance is not necessarily to be understood as a device for private households. On the contrary, the term household appliance may also include equipment for canteen kitchens or dry-cleaning businesses and/or laundry treatment machines and cleaning machines. In the case of such household appliances, the (cleaning) result to be achieved and/or the user-friendliness may be improved in a particularly advantageous manner by the method described.

In general, however, a household appliance may also be understood to be a device such as a food processor, coffee machine or vacuum robot, for which the method described may also be used to advantage in order to improve the work result in a user-friendly manner.

In particular, if the household appliance is a cleaning machine such as a washing machine or a dishwasher, such household appliance will usually use a detergent. This includes not only detergents, but also, in particular, fabric softeners, machine cleaners, dishwashing detergents, water softeners, rinse aids, starches, vinegar cleaners, water repellents, color traps, bleaching agents, graying inhibitors, color transfer inhibitors and/or biologically active systems.

According to an embodiment of the method according to the first aspect, the at least one device performing the method comprises the household appliance and/or a device separate therefrom, in particular a mobile device, which may preferably be installed in the household appliance (i.e. in particular in the treatment room of a washing machine or dishwasher).

For example, the device performing the method is or comprises the household appliance, i.e. in particular a washing machine, a dishwasher or a dryer. If the household appliance itself is designed for this purpose, the method may be performed with a small number of devices and in particular without an additional separate device of the user.

Alternatively, however, an additional and separate device for the household appliance is envisaged. This has the advantage that the method can usually be performed independently of the type and characteristics of the household appliance, which may otherwise not be possible or not to the same extent possible. The separate device is, for example, a mobile (portable) device. The separate device is, for example, a mobile device that may optionally be in communication with the household appliance (for example, wireless network).

However, the separate device may also be a mobile device which may be installed in particular (during operation) in the household appliance, i.e., in the example of a washing machine, it may be installed in the washing machine drum or, in the example of a dishwasher, it may be installed in the interior. Such a separate device is, for example, a dosing device which is designed to deliver a substance (in particular a cleaning agent) to the household appliance. Such a separate device may be in communication with the washing machine, a mobile device and/or a remote server (e.g. to receive the external information).

According to an embodiment of the method according to the first aspect, an external given situation is at least one external given situation for energy costs incurred for the operation of the household appliance. The external information may thus be understood as energy cost information. The external information may for instance be representative for current and/or (expected) future energy costs. For example, a household appliance is (automatically) started at a time when lower or minimal energy costs may be expected for its operation. This may be achieved, for example, by automated counter-cyclical operation (e.g. at night). Similarly, lower or minimal energy costs may be expected if sunny weather reduces the user's energy costs due to photovoltaic systems (for example, by the user). A user preference may also be taken into account, for example, in the form of a time window that is permitted or prohibited for the operation of the household appliance, since a washing machine, for example, should not be operated at night. Taking this information into account may be particularly advantageous for household appliances with high energy consumption (such as washing machines or dishwashers). In this case, the external information is preferably taken into account by influencing the switching on and/or off of the household appliance (or the point in time thereof).

It is also conceivable, however, that the operating program of the household appliance may be adapted to take account of such external information representative of an energy cost-related situation. For example, if high energy costs are expected, an energy-intensive operating mode may be avoided and/or a lower-energy operating mode (e.g. lower washing temperature or an eco or economy program) may be used.

According to an embodiment of the method according to the first aspect, an external given situation of the at least one external given situation is the weather. The external given situation may be regarded as an example of an environmental given situation in so far as it is weather-related. The external information may be regarded as weather-related information in this respect. It has been shown that the effectiveness of household appliances may be improved by considering a weather-related situation.

For example, if the household appliance is a washing machine, weather-related information (e.g. at high temperatures or sultriness) may indicate that the laundry is more sweaty than usual and may be taken into account in the dosage of the detergent and/or the operating mode of the washing machine. In a further example, it may be concluded from the weather-related information (e.g. sunny weather in spring) that there is a high pollen load in the laundry. This may also be taken into account in the dosage of the detergent and/or the operating mode of the washing machine.

According to an embodiment of the method according to the first aspect, the weather-related external given situation is the past, present or future weather. In the case of future weather, the weather-related external given situation refers in particular to the weather after operating the household appliance. On the basis of external information, which is particularly representative of an external given situation relating to the past weather, the condition of the laundry (in the case of a washing machine) (sweaty, pollen-laden, etc.) or (in the case of a vacuum robot) the condition of the floor (soiled with sludge due to rain, pollen-laden, etc.) may be taken into account. External information, which is particularly representative of an external given situation relating to future weather conditions, may be taken into account when operating or controlling the operation of the household appliance, for example by influencing the switching on and/or off of the household appliance (or the point in time thereof). For example, in an example (for a washing machine as a household appliance), switching the washing machine on and/or off (or a point in time thereof) may be influenced so that the laundry may then be dried outside, especially in the sun.

Naturally, the method may also be used to obtain two or more items of information that are representative of two or more external given situations and to operate or control the operation of the household appliance on the basis of these two or more items of information. For example, information on weather-related external given situations may be linked with information on energy costs and a washing machine and any other household appliances may be operated or controlled on the basis of this information. For example, if the weather information indicates that it will not be possible (reliably) to dry washed laundry outdoors in a given future period, the mechanical washing cycle and the necessary subsequent mechanical drying cycle may be carried out in chronological coordination with the energy cost information in such a way that the resulting energy costs are minimized.

According to a further embodiment of the method according to the first aspect the external given situation may be
   the weather condition,
   the weather,
   the climate,
   the temperature,
   the sunshine,
   pollution, especially air pollution,
   the pollen load,
   the humidity,
   the precipitation,
   the wind condition,
   the water hardness at the location where the household appliance is located,
   the address or postcode of the place where the household appliance is located, and/or
   the UV index.
The respective given situation may be a local given situation at the location of the user and/or the location of the household appliance.

The information representative of the external given situation may describe a) a past environment, b) the current environment or, in the form of a prediction, c) a future environment.

The external information may be of a qualitative nature (e.g. representative of whether the sun is shining, whether it is raining, etc.) and/or of a quantitative nature (e.g. representative of how much sunshine, how much rain, etc.).

Weather is understood to be, in particular, the weather or weather condition during a certain period of time (from several days to a season) for a certain area. Weather may be understood as the regional impact of current weather and local climate, especially in relation to tangible weather elements such as precipitation, temperature, wind, air pressure and humidity.

A weather condition is understood to be, in particular, the state of the atmosphere over an area and at a particular time, whereby the weather condition determines the regional weather of the day.

Climate is understood to be the average state of the earth's atmosphere at a given location, which is regularly recurring over a longer period of time (of about 30 years).

Information which is representative of an external given situation in the form of a weather condition, the weather and/or the climate, may in individual cases in particular be representative (qualitatively or quantitatively) of temperature, sunshine, pollution, especially air pollution, pollen load, humidity, precipitation, wind condition and/or the UV index.

As already mentioned, in the example of a washing machine, if the information about a high temperature (which indicates increased sweating), a lot of sunshine (which indicates outdoor activities and thus also increased sweaty or dirty laundry or a high allergen load) is known, the type of detergent, the amount of detergent and/or the operating mode of the washing machine may be adjusted. As already mentioned, also in the example of a washing machine, if the information about wind and/or sun conditions is known, the household appliance may be switched on and/or off in such a way that the laundry may be dried outside.

The (weather-related) given situation described may, for example, relate to the location or surroundings of the household appliance and/or to the location or surroundings of the user of the household appliance.

As described above, it is also possible that the external given situation may not necessarily be a given situation of an outdoor environment, but may also be a given situation of an indoor environment, e.g. room temperature. Such information may be taken into account—in the case of a dishwasher, for example—to the extent that the dishwasher is operated more frequently at high temperatures in order to prevent odor and/or hygiene problems.

As already mentioned, such external information may be obtained, for example, by receiving it from a server providing such information. Alternatively, or in addition, it is conceivable that such external information may be received, for example, from a user's private weather station (which is integrated, for example, in a SmartHome system).

According to a further embodiment of the method according to the first aspect, an external given situation of the at least one external given situation is an odor condition, and the external information may therefore be regarded as odor information. It has been found that taking an odor condition as an example of an environmental condition may positively influence the effectiveness of the result to be achieved with the household appliance. If the external odor condition indicates, for example, an (undesirable) odor, the operation of the household appliance or the control thereof is adjusted, for example, in such a way that—in the case of a washing machine or a tumble dryer—fragrances, more fragrances and/or other odorants are added during operation.

According to a further embodiment of the method according to the first aspect, an external given situation of the at least one external given situation is a property of water to be used for operating the household appliance. In an example, the property of the water is the water hardness or the pH value of the water. An external information representative of this may be taken into account in the operation of the household appliance, for example by influencing a type and/or dosage of a detergent to be used.

According to a further embodiment of the method according to the first aspect, an external given situation of at least one external given situation is the presence or consumption of a type of food. The external information in this respect may be considered as food information. In the case of a given situation relating to the presence of food, the external information may be representative, for example, of what food is available, for example in a refrigerator. This information may, for example, be provided by a smart refrigerator (as part of a SmartHome system). This information may also be obtained, determined and provided on the basis of the food purchases made by the user. This type of information may be provided particularly easily by the service provider or an account of the user, especially in the context of food purchased online and/or delivered. In the case of a given situation relating to the consumption of food, the external information may, for example, be representative of the food that has been prepared. This information may be provided, for example (in the context of a SmartHome system), by an intelligent food processor or other possibly thermal treatment device (e.g. an oven), for example based on the recipes used by the user. If the dishwasher is then operated at a time interval to be determined, it is to be assumed that objects with which the processed food has come into contact are in the dishwasher. The dishwasher may then adjust the cleaning program and the type and quantity of detergent used, taking into account the level of soiling (food residues).

In other words, the previous remarks may be summarized as follows and described with regard to some particularly preferred embodiments:

As stated above, a first aspect of the present disclosure is a method for operating or controlling an operation of a household appliance (100, 300) performed by at least one device (100, 200, 300, 400) comprising:
- obtaining (510) external information representative of at least one external given situation outside the household appliance (100, 300); and
- operating (520) or controlling an operation of the household appliance (100, 300) at least in consideration of the external information received.

As also stated above, the external given situation may describe representative information about a) a past environment, b) the current environment or, in the form of a prediction, c) a future environment.

Naturally, more than one item of external information may be taken into account for operating or controlling the operation of a household appliance (100, 300).

For a typical household appliance (100, 300) such as a textile washing machine, for example, the following process chain provides external information, which may subsequently be linked to information chains:
i) Food purchase→food storage→food processing→food consumption→occurrence of stains/soiling on textiles (e.g. clothing or household textiles such as dish towels or tablecloths).

For example, if the external information is representative of the soiling of textiles, e.g. in the form of a color value on the textiles, then by combining this external information with other external information, e.g. the nature of the textiles and the foodstuff purchased or processed in a defined period of time beforehand, a well-founded estimate of the chemical nature of this soiling is possible.

If, for example, a shirt has a red stain and cherries have been purchased or processed several times in the past seven days, but no other red-dying foods have been purchased or processed, there is an increased probability that the red stain is cherry juice.

According to a further embodiment of the method according to the first aspect, an external given situation of at least one external given situation is a geographical location of the household appliance and/or a user. External information representative of the geographical location of the household appliance may be used to take into account, for example, social background and/or cultural habits (such as increased or decreased consumption of certain foods, for example tea/coffee). Such information may then be taken into account, in particular in the case of a washing machine, for example to influence the selection, composition and/or dosage of a detergent to be used for the household appliance and/or the mode of operation of the household appliance.

External information representative of the geographical location of the user may in particular indicate certain activities (such as sporting or travel activities) of the user. In the example of a washing machine, such external information obtained may then be taken into account in the operation or control of the operation of the household appliance, for example to influence the selection, composition and/or dosage of a cleaning product to be used for the household appliance and/or the mode of operation of the household appliance. External information representative of the user's geographical location may also be used to switch the household appliance on or off when the user arrives at or leaves the location of the household appliance.

According to a further embodiment of the method, an external given situation of the at least one external given situation is a user activity, in particular a travel activity, a sports activity and/or a purchasing activity. Thus, such a given situation does not refer to the surroundings of the household appliance ("surroundings condition") but to the activity of the user ("activity condition"). As already mentioned, such external information may in particular be used to influence the switching on and/or off of the household appliance, the selection, composition and/or dosage of a cleaning product to be used for the household appliance and/or the mode of operation of the household appliance.

Such external information representative of an activity condition may be obtained, for example, because it may be provided based on a (digital) calendar of the user. In this respect, the external information may include calendar data representative of an activity situation of the user. Such external information may also be obtained by providing it on the basis of fitness data (e.g. a fitness tracker, a mobile phone or a smartwatch). In this respect, the external information may include fitness data that is representative of the user's activity.

Furthermore, the method according to the first aspect may also include obtaining CRM information related to the user of the household appliance (which is representative of the user's preferences or habits, for example with regard to the cleaning product). The operation or control of the operation of the household appliance may then also take into account the CRM information received.

According to a further embodiment of the method according to the first aspect, the received external information influences
- switching the household appliance on and/or off,
- selecting, combining and/or dosing a cleaning product to be used for the household appliance, and/or
- an operating mode of the household appliance.

The operation or control of an operation of the household appliance, taking into account the external information received, is therefore particularly effective in influencing these actions.

With regard to switching the household appliance on and/or off, you may, for example, influence whether (at all) the household appliance is switched on and/or off and/or at what time (time, date) the household appliance is switched on and/or off. As mentioned above, switching the household appliance on and/or off may preferably be influenced based on an external given situation, which is a geographical location of the household appliance and/or a user, but also based on an external given situation related, for example, to the weather.

Influencing the selection, composition and/or dosage of a detergent to be used for the household appliance may be accomplished by various actions. For example, the amount to be dosed (the amount of detergent in the case of a washing machine or the amount of rinse aid in the case of a dishwasher), the dosing time, the product to be dosed or individual ingredients (for example soil removing polymers, bleaching agents, enzymes, sanitary rinse aid in the case of a washing machine) or combinations thereof may be influenced. In addition, the compatibility of combinations of ingredients may be taken into account to avoid incompatibility (e.g. bleaching agents and enzymes).

Influencing the operating mode of the household appliance may, for example, include selecting a certain (preset) program, running additional programs, influencing (extending or shortening) the program run time, changing individual program parameters (in the case of a washing machine, for example, temperature, spin speed, etc.).

In addition, it is possible not only to operate or control the operation of the household appliance (automated) taking into account the external information received, but also to give the user a recommendation. For example, it may be possible that manual preliminary treatment (e.g. of clothing, crockery or flooring) may be necessary in addition to automated adjustment of the household appliance. Such a recommendation may then, for example, be displayed to the user by employing a user interface on an output device.

According to a further preferred embodiment of the method, the method also includes the request and/or receipt of information representative of the quality (e.g. user satisfaction) of the result achieved by the household appliance. Obtaining this information may be automated (e.g. by the household appliance). This may be achieved, for example, by employing sensors (e.g. optical sensors to detect the result, in the case of a washing machine, for example, sensors to detect the degree of soiling of the laundry or rinse water). Alternatively or in addition, this information may also be requested from the user (for example by the household appliance or a separate device such as a smartphone) afterwards. In an example, the information may be included in a user profile representative of the quality of the result achieved by the operation.

On the basis of the information obtained representative of the quality of the result obtained by the household appliance and/or by recording parameters used by the household appliance (in the case of a washing machine, for example, the quantity of detergent composition to be dispensed, the short bath ratio, the temperature, the duration, the amount of water, the speed of rotation, etc.), the operation of the household appliance may preferably be optimized according to the external given situation.

In this context in particular, it is possible that the optimization of the operation of the household appliance includes or is based on machine learning, so that the highest possible quality of the result obtained is achieved for a given external given situation. Machine learning is understood to mean that an artificial system (e.g. a device according to the second aspect or a system according to the third aspect) learns from examples and may generalize these after the learning phase is completed. This means that the examples are not simply learned by heart, but patterns and regularities in the learning data are recognized. Different approaches may be taken to this end. For example, supervised learning, partially supervised learning, unsupervised learning, reinforced learning and/or active learning may be used, especially in combination with deep learning methods. For instance, supervised learning may be performed using an artificial neural network (such as a recurrent neural network) or a support vector machine. Unsupervised learning may also be performed using an artificial neural network (e.g. an auto encoder). The learning data used are, for example, the information received (repeatedly) representative of the quality of the result obtained, the external information representative of an external given situation outside the household appliance and/or the parameters used in the household appliance.

According to a second aspect, in addition, a device is described which is set up or includes appropriate means to implement and/or control an exemplary method according to the first aspect.

An exemplary device comprises, for example, at least one processor and at least one memory with computer program code, wherein the at least one memory and the computer program code are configured to execute and/or control with the at least one processor at least one exemplary method according to the first aspect. A processor is to be understood, for example, as a control unit, a microprocessor, a micro-control unit such as a micro-controller, a digital signal processor (DSP), an application-specific integrated circuit (ASIC) or a field programmable gate array (FPGA).

For example, an exemplary device further comprises features for storing information such as a program memory and/or a main memory. For example, exemplary devices further each comprise features for receiving and/or sending information via a network such as a network interface. For example, exemplary devices are interconnected and/or connectable via one or more networks.

An exemplary device is or comprises, for example, data processing equipment which is set up in terms of software and/or hardware to be able to carry out the respective steps of an exemplary method. The data processing equipment may, for example, be the household appliance or a part thereof. The data processing equipment may also be separate from the domestic appliance. Examples of such equipment are a computer, a desktop computer, a server, a thin client and/or a portable computer (mobile device), such as a laptop computer, a tablet computer, a wearable, a personal digital assistant or a smartphone. Similarly, in an example, the data processing equipment may be designed to be placed in the household appliance (i.e. in particular in the treatment room).

An exemplary device may also comprise (at least) a user interface, (at least) a communication interface (in particular for wireless communication with the household appliance or another device), and/or (at least) a sensor device which may detect parameters of the household appliance (in particular during operation).

Furthermore, an exemplary computer program as contemplated herein is described which comprises program instructions which cause a processor to execute and/or control an exemplary method as contemplated herein when the computer program is running on the processor.

Furthermore, an exemplary computer-readable storage medium as contemplated herein is described which contains an exemplary computer program as contemplated herein.

According to a third aspect, a system is further described comprising several devices, in particular the household appliance and a further device separate therefrom, which are adapted to perform together a method according to the first aspect. The further device may be, for example, a mobile device or a server.

The exemplary embodiments of the present disclosure described above in this description should also be understood as disclosed in all combinations with each other. In particular, exemplary embodiments should be understood in terms of the different aspects disclosed.

In particular, the prior or subsequent description of method steps according to preferred embodiments of a method should also reveal corresponding features for performing the method steps by preferred embodiments of a device. Likewise, by the disclosure of employing a device for carrying out a method step, the corresponding method step shall also be disclosed.

Further advantageous exemplary embodiments of the present disclosure may be found in the following detailed description of some exemplary embodiments of the present disclosure, especially in connection with the Figures. However, the Figures are only intended to clarify, but not to determine the scope of protection of the present disclosure. The Figures are not to scale and are merely intended to illustrate the general concept of the present disclosure. In particular, features contained in the Figures are not intended to be considered as a necessary part of the present disclosure.

BRIEF DESCRIPTION OF THE DRAWINGS

The present disclosure will hereinafter be described in conjunction with the following drawing figures, wherein like numerals denote like elements, and.

In the drawings the following is shown.

Figure 1:
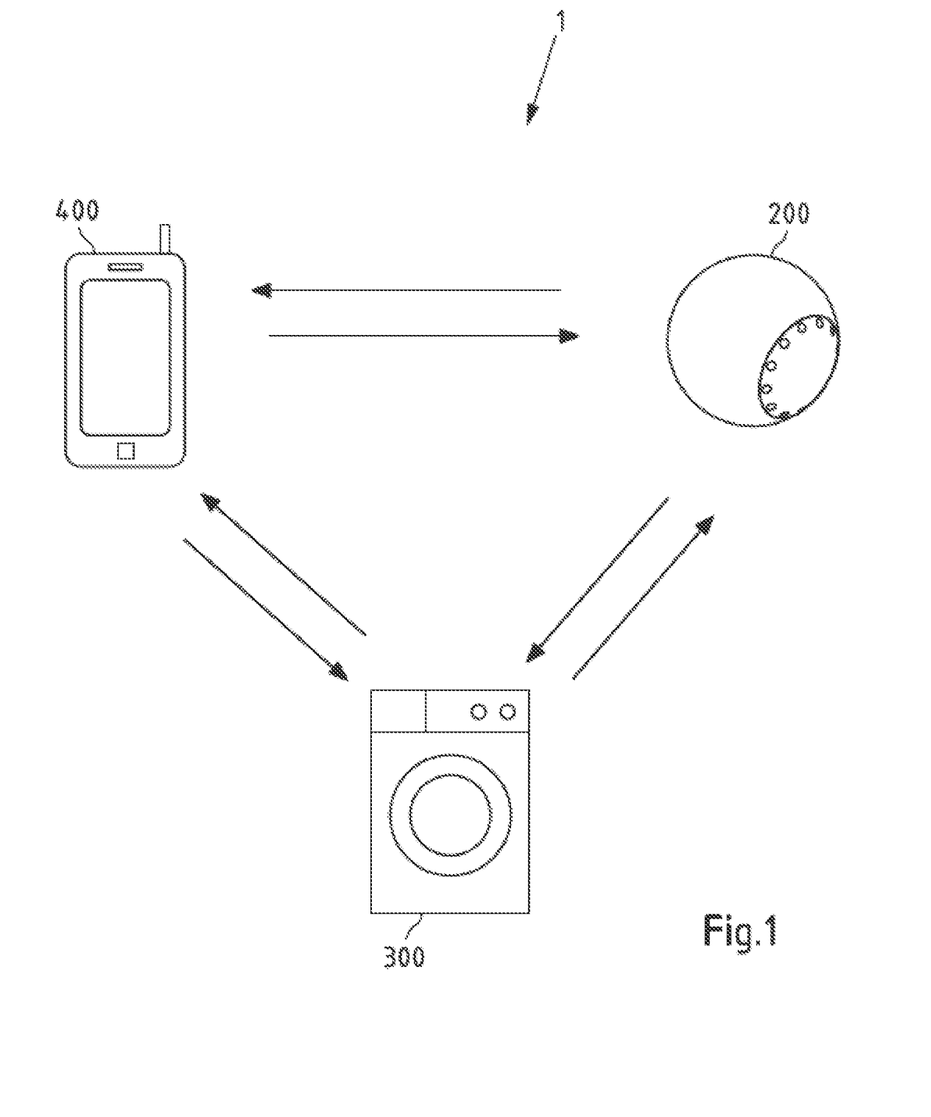
FIG. 1 is a schematic diagram of an exemplary embodiment of a system as contemplated herein.

FIG. 1 shows first of all a schematic diagram of an exemplary embodiment of a System 1 as contemplated herein comprising the devices 200, 300 and 400. The system is designed to carry out exemplary methods as contemplated herein. Device 200 is an exemplary mobile device 200, which in this case may be installed in the treatment room of the household appliance 300 (here exemplarily shown as a washing machine). Both the device 200 and the washing machine 300 may each be a device as contemplated herein. Furthermore, System 1 comprises the mobile device 400 in the form of a smartphone as a further device. Mobile device 400 may also be a device as contemplated herein or may perform individual steps of exemplary methods as contemplated herein. However, device 400 may also be a computer, a desktop computer or a portable computer, such as a laptop computer, a tablet computer, a personal digital assistant (PDA) or a wearable. In addition or as an alternative to devices 300 and 400, the system may also include a server (not shown). It is also conceivable that System 1 may also include fewer or more than three devices.

While the examples given here are described in particular in connection with a household appliance in the form of a washing machine 300, the explanations also apply mutatis mutandis to other types of household appliances.

Each of the devices 200, 300, 400 may have a communication interface to communicate with one or more of the other devices to transmit and/or to exchange information.

Figure 2:
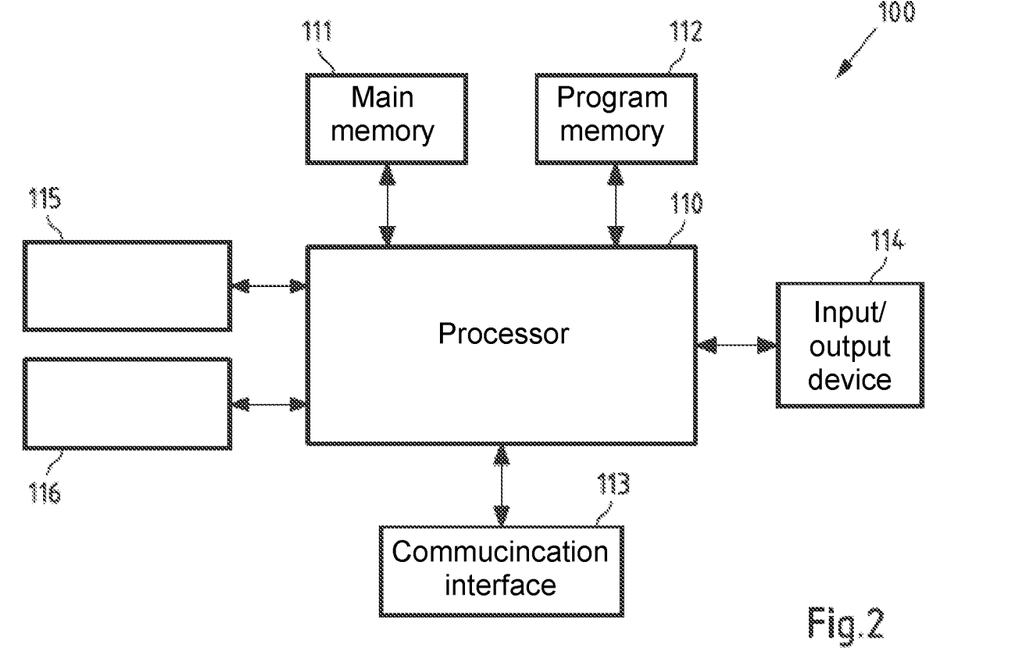
FIG. 2 is a block diagram of an exemplary embodiment of a device as contemplated herein for carrying out an exemplary embodiment of a method as contemplated herein.

FIG. 2 now shows a block diagram of an exemplary embodiment of a device 100 as contemplated herein for carrying out an exemplary embodiment of a method as contemplated herein. Device 100 in FIG. 2 may be an example for device 200 shown in FIG. 1, the washing machine 300 shown or the mobile device 400 (or a part thereof) shown.

Processor 110 of device 100 is designed in particular as a microprocessor, micro-control unit, micro-controller, digital signal processor (DSP), application-specific integrated circuit (ASIC) or field programmable gate array (FPGA).

Processor 110 executes program instructions which are stored in program memory 112 and stores, for example, intermediate results or the like in the working or main memory 111. For example, program memory 112 is a non-volatile memory such as a flash memory, a magnetic memory, an EEPROM memory (electrically erasable programmable read-only memory) and/or an optical memory. Main memory 111 is, for example, a volatile or non-volatile memory, in particular a random access memory (RAM) such as a static RAM memory (SRAM), a dynamic RAM memory (DRAM), a ferro-electric RAM memory (FeRAM) and/or a magnetic RAM memory (MRAM).

Program memory 112 is preferably a local data storage device permanently connected to device 100. Data storage devices attached to device 100 are, for example, hard disks integrated in device 100. Alternatively, the data storage device may also be a data storage device that may be disconnected from device 100.

Program memory 112 contains, for example, the operating system of device 100, which is at least partially loaded into main memory 111 and executed by processor 110 when device 100 is started. In particular, when device 100 is started, at least part of the kernel of the operating system is loaded into main memory 111 and executed by processor 110.

In particular, the operating system enables the use of device 100 for data processing. For example, it manages resources such as main memory 111 and program memory 112, communication interface 113, input and output device 114, provides other programs with basic functions through programming interfaces, and controls the execution of programs.

Processor 110 also controls communication interface 113, which may be, for example, a network interface and may be configured as a network card, network module and/or modem. Communication interface 113 is set up in particular to establish a connection between device 100 and other devices, in particular via a (wireless) communication system, for example a network, and to communicate with these devices. Communication interface 113 may, for example, receive data (via the communication system) and forward the data to processor 110 and/or receive data from processor 110 and send the data (via the communication system). Examples of a communication system are a local area network (LAN), a wide area network (WAN), a wireless network (e.g. according to IEEE 802.11 standard, Bluetooth (LE) standard and/or NFC standard), a wired network, a mobile network, a telephone network and/or the Internet. For example, communication with the Internet and/or other devices may be established using communication interface 113. In the case of the devices 200, 300, 400, the respective communication interface 113 may be used to communicate with the respective other devices 200, 300, 400 or the Internet.

In particular, such a communication interface 113 may be used to receive external information representative of at least one external given situation outside household appliance 300. Furthermore, the components shown (and other components, if required) may be used to operate or control the operation of household appliance 300, taking into account the external information received.

This is described in more detail in connection with FIG. 5.

Furthermore, processor 110 may control at least one input/output device 114. Input/output device 114 is, for example, a keyboard, a mouse, a display unit, a microphone, a touch-sensitive display unit, a speaker, a reader, a drive and/or a camera. For example, input/output device 114 may receive input from a user and forward it to processor 110 and/or receive and output information for the user from processor 110.

Finally, device 100 may include other components 115, 116 which are indicated here and not specified in more detail. Such a component may be, for example, a GPS module in order to obtain location data of the corresponding device. The location data may represent external information representative of at least one external given situation outside the household appliance 300, whereby the given situation may be, for example, the geographical location of the household appliance 300 or the mobile device 400 and thus of the user.

A further example of a component 115, 116 is a temperature sensor to obtain temperature data. Temperature data may also represent external information representative of at least one external given situation outside household appliance 300 in the form of room temperature.

Figure 3:
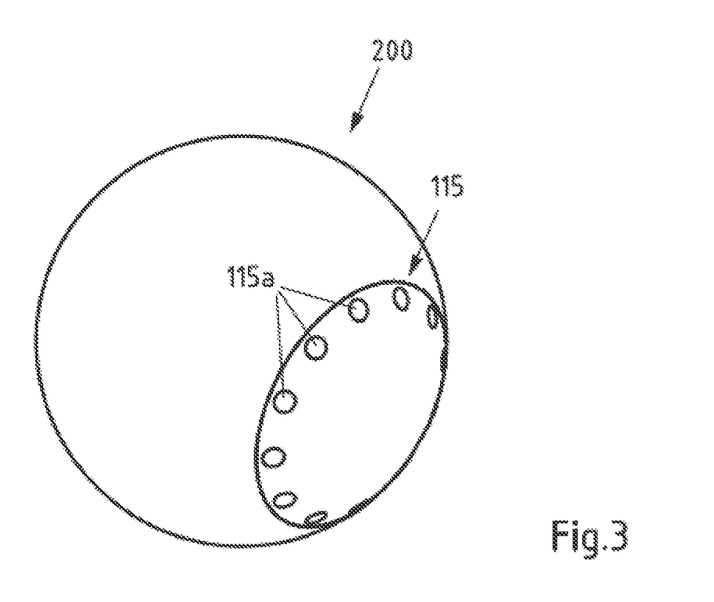
FIG. 3 is a schematic diagram of the illumination detecting device shown in FIG. 1 in perspective view.

FIG. 3 now shows a schematic diagram of appliance 200 from FIG. 1 in perspective view. Appliance 200 is a separate appliance from washing machine 300. Appliance 200 has an essentially spherical, watertight casing, which is at least partially made of a non-rigid or elastic material. For example, device 200 comprises a supply of detergent or individual detergent components to be combined as required (not shown). The detergent or the individual detergent components may be dispensed into the interior of washing machine 300 via pump unit 115 via the outlet openings 115*a* during the operation of washing machine 300. This is because device 200 is designed to be installed in the laundry drum of washing machine 300 and to be freely mixed with the laundry.

Device 200 may also be designed to send control signals to washing machine 300, for example to influence the program sequence of washing machine 300.

Figure 4:
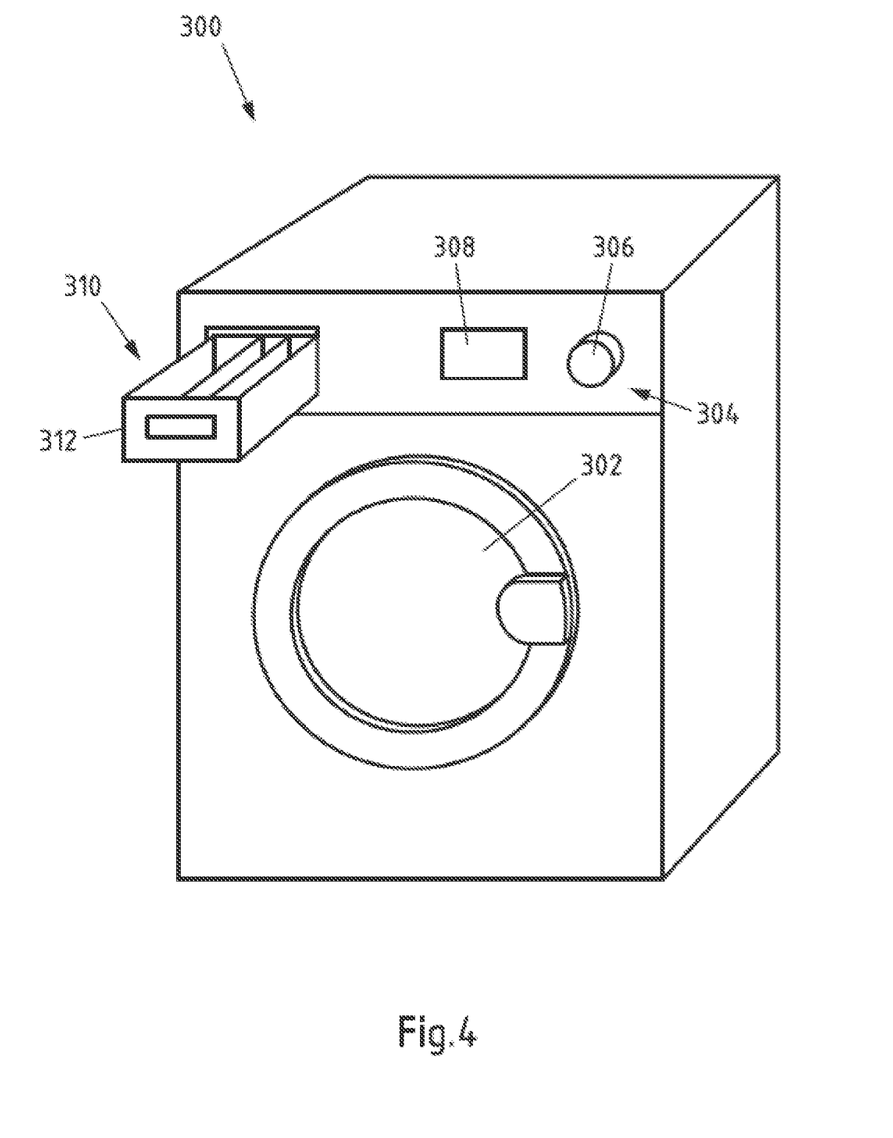
FIG. 4 is a schematic diagram of the washing machine shown in FIG. 1 in perspective view.

FIG. 4 shows a schematic diagram of washing machine 300 from FIG. 1 in perspective view. Device 100 shown in FIG. 2 is in this case washing machine 300 or integrated into it. Washing machine 300 in this case is an automatic household washing machine for textiles, which is designed as a front-loading washing machine (front loader) in which a laundry drum 302 rotates around a horizontal axis. However, the use of other types of cleaning devices is also conceivable. In addition to the drum 302, washing machine 300 comprises user interfaces 304 in the form of a control element 306 and a display element 308. Control element 306 is designed as a rotary knob and may be used to set various washing parameters, for example, the washing program and/or the washing temperature. Display element 308 visually displays information for the user. However, washing machine 300 may also feature other user interfaces. Washing machine 300 also comprises a dispenser 310, which includes a dispenser drawer 312. This is used to hold a cleaning agent.

Washing machine 300 may also feature a detergent supply, which is automatically dosed.

Figure 5:
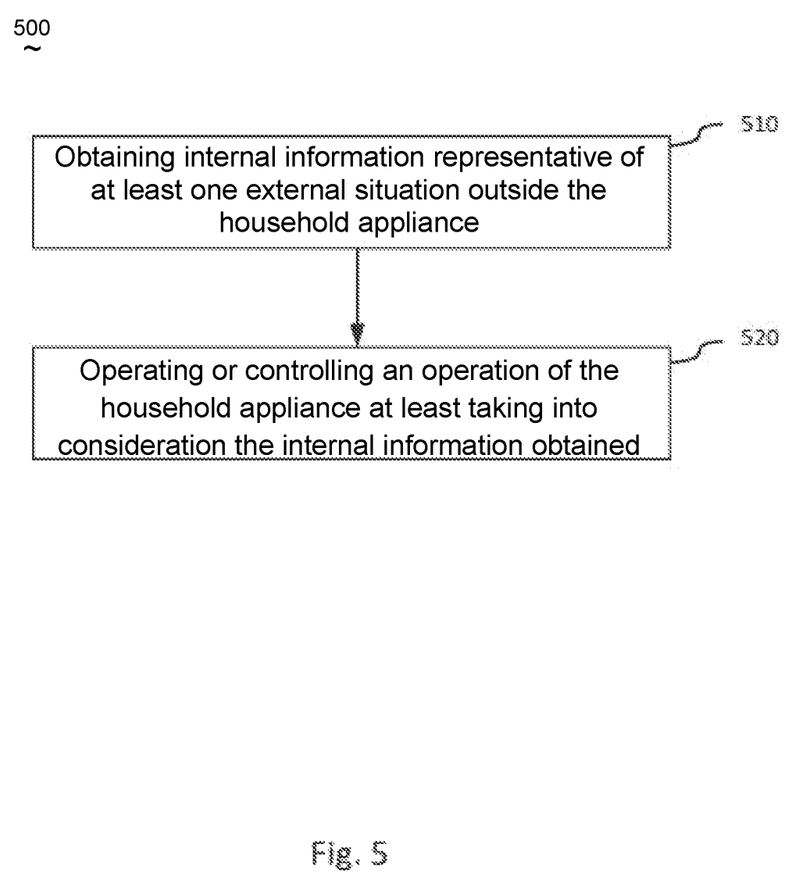
FIG. 5 is a flowchart of an exemplary embodiment of a method as contemplated herein.

FIG. 5 shows a flow chart 500 of an exemplary embodiment of an exemplary method.

First, external information representative of at least one external given situation outside household appliance 300 is obtained (step 510), e.g. external information may be obtained (received) from device 200, household appliance 300 and/or mobile device 400. The corresponding external information may be determined in an example based on sensors of the device. In another example, the external information may be obtained from the Internet (e.g. from a server, for example in the case of weather information). In a further example, the external information may also be based on calendar data (e.g. of the mobile device) 400. The external information may also be representative for several external given situations. An external given situation may be, for example:

- energy costs incurred for the operation of the household appliance;
- the (past or future) weather (in the area of the household appliance), especially after the household appliance has been in operation;
- the weather condition, the weather, the climate, the temperature, the sunshine, the pollution, in particular air pollution, pollen load, humidity, precipitation, wind conditions and/or UV index;
- an odor condition;
- a property of water to be used for operating household appliance 300;
- the presence or consumption of the type of food;
- a geographical location of household appliance 300 and/or a user;
- a user activity, in particular a travel activity, a sporting activity and/or a purchasing activity.

Subsequently, household appliance 300 will be operated or the operation of household appliance 300 will be controlled, at least taking into account the external information received (Action 520). The external information may, for example, influence the following exemplary steps in the operation of household appliance 300:

- switching household appliance 300 on and/or off;
- selecting, assembling and/or dosing a detergent to be used with household appliance 300;
- an operating mode of household appliance 300.

In particular, the operating steps to be adjusted depend on the external information and the type of household washing machine 300. Ultimately, however, the result to be achieved by household appliance 300 may be improved in a user-friendly manner.

Figure 6:
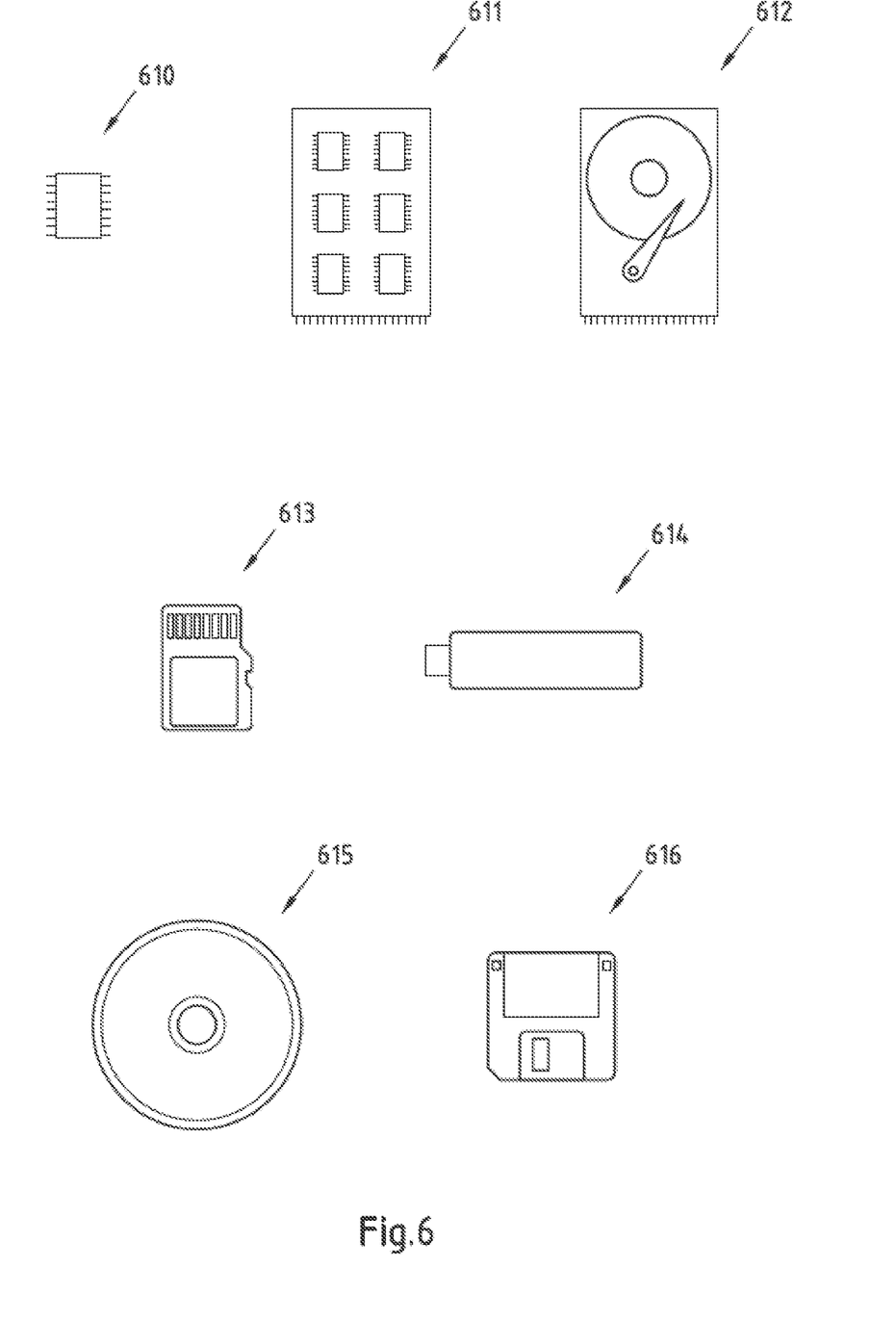
FIG. 6 are different exemplary embodiments of a storage medium.

Finally, FIG. 6 shows different exemplary embodiments of storage media on which an embodiment of a computer program as contemplated herein may be stored. The storage medium may be, for example, a magnetic, electrical, optical and/or other type of storage medium. The storage medium may be, for example, part of a processor (e.g., processor 110 of FIG. 2), for example, a (non-volatile or volatile) program memory of the processor or a part thereof (such as program memory 112 in FIG. 2). Exemplary embodiments of a storage medium are a flash memory 610, an SSD hard disk 611, a magnetic hard disk 612, a memory card 613, a memory stick 614 (e.g. a USB stick), a CD-ROM or DVD 615 or a floppy disk 616.

The exemplary embodiments of the present disclosure described in this specification and the optional features and properties mentioned in each case shall be understood to be disclosed in all combinations with each other. In particular, unless explicitly stated otherwise, the description of an exemplary embodiment of a feature shall not be understood in the present case to mean that the feature is indispensable or essential for the function of the exemplary embodiment.

The sequence of method steps described in this specification is not mandatory; alternative sequences of method steps are conceivable. The method steps may be implemented in different ways, e.g. implementation in software (by program instructions), hardware or a combination of both for implementing the method steps.

Terms used in the Claims such as "comprising", "having", "containing", "including" and the like do not exclude further elements or steps. The expression "at least partially" covers both the "partially" case and the "complete" case. The wording "and/or" should be understood to mean that both the alternative and the combination should be disclosed, i.e. "A and/or B" means "(A) or (B) or (A and B)". The use of the indefinite article does not exclude a plural. A single device may perform the functions of several units or devices mentioned in the Claims. Reference signs indicated in the Claims are not to be regarded as limitations of the means and steps used.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for controlling an operation of a laundry treatment machine performed by at least one device, the method comprising:
   obtaining external information representative of at least a weather condition, outside the laundry treatment machine, the weather condition being indicative of an odor condition, and
   controlling the operation of the laundry treatment machine in response to the external information received.

2. The method according to claim 1, further comprising adjusting a dosage of detergent in response to the external information.

3. The method according to claim 1, wherein at least one device carries out the method comprises one of the laundry treatment machine and a device separate therefrom.

4. The method according to claim 1, wherein the external information further includes energy costs incurred for operating the laundry treatment machine.

5. The method according to claim 1, wherein the external information further includes pollen-count.

6. The method according to claim 5, wherein the weather condition includes one of past weather and future weather.

7. The method according to claim 1, wherein the external information includes
   climate,
   temperature,
   sunshine,
   pollution,
   pollen load,
   humidity,
   precipitation,
   water hardness at the location where the household appliance is located,
   address or postcode of a location where the household appliance is located,
   wind condition,
   UV index and combinations thereof.

8. The method according to claim 1, wherein the exterior information includes an odor condition.

9. The method according to claim 1, wherein an external information includes a property of water to be used for operating the laundry treatment machine.

10. The method according to claim 1, wherein an external information includes a presence or consumption of a type of food.

11. The method according to claim 1, wherein an external information includes a geographical location of the laundry treatment machine.

12. The method according to claim 1, wherein an external information includes a user activity.

13. The method according to claim 1, wherein the external information includes
   switching the household appliance off,
   selecting, assembling, dosing a detergent to be used for the household appliance, and
   an operating mode of the laundry treatment machine.

14. A method for controlling the operation of laundry treatment machine performed by at least one device the method comprising:
   obtaining external information representative of a weather condition outside the laundry treatment machine, the weather condition being indicative of an odor condition in clothing being washed, and
   controlling the operating condition of the laundry treatment machine including the amount of detergent in response to the weather condition.

15. The method according to claim 14, wherein the external information includes a geographic location.

* * * * *